(12) United States Patent
Siladie et al.

(10) Patent No.: US 10,302,553 B2
(45) Date of Patent: May 28, 2019

(54) GAS EXHAUST BY-PRODUCT MEASUREMENT SYSTEM

(71) Applicant: Lam Research Corporation, Fremont, CA (US)

(72) Inventors: Cristian Siladie, San Ramon, CA (US); Luc Albarede, Fremont, CA (US); Yassine Kabouzi, Fremont, CA (US); Edward J. McInerney, San Jose, CA (US); Sassan Roham, San Ramon, CA (US)

(73) Assignee: Lam Research Corporation, Fremont, CA (US)

( * ) Notice: Subject to any disclaimer, the term of this patent is extended or adjusted under 35 U.S.C. 154(b) by 0 days.

(21) Appl. No.: 15/691,405

(22) Filed: Aug. 30, 2017

(65) Prior Publication Data
US 2019/0064057 A1    Feb. 28, 2019

(51) Int. Cl.
G01N 21/15      (2006.01)
G01N 21/3504   (2014.01)
H01L 21/67      (2006.01)

(52) U.S. Cl.
CPC ......... *G01N 21/15* (2013.01); *G01N 21/3504* (2013.01); *H01L 21/67017* (2013.01); *H01L 21/67253* (2013.01); *G01N 2021/151* (2013.01); *H01L 21/67069* (2013.01)

(58) Field of Classification Search
CPC .......................... G01N 21/15; G01N 21/3504
See application file for complete search history.

(56) References Cited

U.S. PATENT DOCUMENTS

| 5,463,460 A * | 10/1995 | Fishkin | G01N 21/15 356/339 |
| 5,830,807 A | 11/1998 | Matsunaga et al. | |
| 5,966,586 A | 10/1999 | Hao | |
| 6,336,841 B1 | 1/2002 | Chang et al. | |
| 9,735,069 B2 | 8/2017 | Kabouzi et al. | |
| 2005/0081881 A1* | 4/2005 | Skeidsvoll | B08B 7/0042 134/1 |
| 2006/0139647 A1* | 6/2006 | Tice | G01N 21/15 356/437 |

(Continued)

OTHER PUBLICATIONS

Albarede et al., U.S. Appl. No. 14/862,983, filed Sep. 23, 2015.

(Continued)

*Primary Examiner* — Errol V Fernandes
(74) *Attorney, Agent, or Firm* — Beyer Law Group LLP

(57) ABSTRACT

A gas exhaust by-product measurement system is provided. A gas chamber is configured to receive exhaust from the exhaust output. A light source, light detector, and at least one optical element are positioned so that a light beam from the light source is directed to the at least one optical element a plurality of times before reaching the light detector. At least one heater provides heat to the at least one optical element. A plurality of purge gas nozzles are in fluid connection with the optical cavity. A high flow line is in fluid connection between a purge gas source and the plurality of purge gas nozzles. A low flow line is in fluid connection between the purge gas source and the plurality of purge gas nozzles. At least one flow controller manages a plurality of flow rates including a high flow and a low flow.

16 Claims, 6 Drawing Sheets

(56) References Cited

U.S. PATENT DOCUMENTS

| | | | |
|---|---|---|---|
| 2006/0219957 A1* | 10/2006 | Ershov | B82Y 10/00 250/504 R |
| 2009/0014409 A1 | 1/2009 | Grimbergen | |
| 2009/0045167 A1 | 2/2009 | Maruyama | |
| 2010/0114836 A1 | 5/2010 | Chan et al. | |
| 2010/0190098 A1 | 7/2010 | Walker et al. | |
| 2010/0327192 A1* | 12/2010 | Fomenkov | H01S 3/2232 250/504 R |
| 2012/0242989 A1 | 9/2012 | So et al. | |
| 2012/0312973 A1* | 12/2012 | D'Costa | G01N 21/15 250/239 |
| 2013/0193108 A1 | 8/2013 | Zheng et al. | |
| 2014/0204382 A1 | 7/2014 | Christensen | |
| 2014/0295082 A1 | 10/2014 | Motoyama et al. | |
| 2016/0139038 A1 | 5/2016 | Oldsen et al. | |
| 2016/0172191 A1 | 6/2016 | Hirano | |
| 2017/0084426 A1 | 3/2017 | Albarede et al. | |
| 2017/0084503 A1 | 3/2017 | Kabouzi et al. | |
| 2017/0087606 A1 | 3/2017 | Nakamura et al. | |

OTHER PUBLICATIONS

Kabouzi et al., U.S. Appl. No. 14/863,211, filed Sep. 23, 2015.
Office Action from U.S. Appl. No. 14/862,983 dated Jul. 29, 2016.
Final Office Action from U.S. Appl. No. 14/862,983 dated Feb. 10, 2017.
Notice of Allowance from U.S. Appl. No. 14/862,983 dated Jul. 5, 2017.
International Search Report dated Nov. 26, 2018 from International Application No. PCT/US2018/045428.
Written Opinion dated Nov. 26, 2018 from International Application No. PCT/US2018/045428.

* cited by examiner

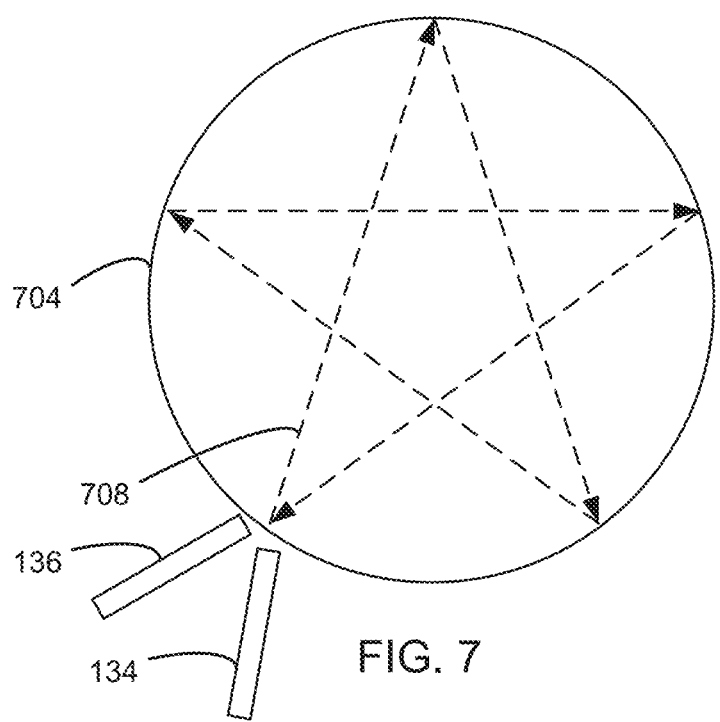

GAS EXHAUST BY-PRODUCT MEASUREMENT SYSTEM

CROSS REFERENCE TO RELATED APPLICATIONS

The present disclosure is related to U.S. patent application Ser. No. 14/863,211 entitled "APPARATUS FOR DETERMINING PROCESS RATE" by Albarede et al., filed on Sep. 23, 2015, which is incorporated by reference for all purposes.

BACKGROUND

The present disclosure relates to the manufacturing of semiconductor devices. More specifically, the disclosure relates to etching used in manufacturing semiconductor devices.

During semiconductor wafer processing, silicon containing layers are selectively etched. During the etching of silicon containing layers, it is desirable to measure etch rate, etch CD, etch profile, and etch uniformity from wafer to wafer or chamber to chamber. IR absorption may be used to measure the concentration of a by-product produced by the etch process. Etch by-products, dust, and other contaminants may deposit on optical elements, reducing the accuracy of the measurement of IR absorption, reducing the accuracy of the measurement of by-product concentration. It is desirable to maintain the accuracy of the measurement of by-product concentration.

SUMMARY

To achieve the foregoing and in accordance with the purpose of the present disclosure, a gas exhaust by-product measurement system, attachable to an exhaust output from an exhaust pump of a processing chamber is provided. A gas chamber is configured to receive exhaust from the exhaust output, where the gas chamber further includes an optical cavity, wherein exhaust passes through the optical cavity. A light source, light detector, and at least one optical element are positioned so that a light beam from the light source is directed to the at least one optical element a plurality of times before reaching the light detector. At least one heater provides heat to the at least one optical element, so that the at least one optical element is heated by an at least one heater. A plurality of purge gas nozzles are in fluid connection with the optical cavity. A high flow line is in fluid connection between a purge gas source and the plurality of purge gas nozzles. A low flow line is in fluid connection between the purge gas source and the plurality of purge gas nozzles, wherein at least part of the low flow line is in parallel to the high flow line. At least one flow controller manages a plurality of flow rates including a high flow and a low flow.

In another manifestation, a method for processing a substrate in a processing chamber is provided. The substrate is dry processed, wherein the dry processing creates at least one gas by-product. The at least one gas by-product is pumped out of the processing chamber through an exhaust pump into a gas cell, wherein the gas cell comprises at least one optical element. A concentration of the at least one gas by-product in the gas cell is measured. The at least one optical element is heated. A low flow purge gas is provided to the at least one optical element. A pulsed high flow purge gas is provided to the at least one optical element.

In another manifestation, a gas by-product measurement system attachable to an exhaust output from an exhaust pump of a processing chamber is provided. A gas chamber is configured to receive exhaust from the exhaust output and includes an optical cavity, where exhaust passes through the optical cavity. A light source, a light detector, and at least one optical element are positioned so that a light beam from the light source is directed to the at least one optical element a plurality of times before reaching the light detector. At least one heater provides heat to the at least one optical element, so that the at least one optical element is heated by an at least one heater. A purge gas source provides a purge gas flow of no more than 6000 sccm. A plurality of purge gas nozzles is in fluid connection between the optical cavity and the purge gas source.

These and other features of the present disclosure will be described in more detail below in the detailed description of the disclosure and in conjunction with the following figures.

BRIEF DESCRIPTION OF THE DRAWINGS

The present disclosure is illustrated by way of example, and not by way of limitation, in the figures of the accompanying drawings and in which like reference numerals refer to similar elements and in which:

FIG. 7 is a schematic view of another embodiment of a gas cell.

DETAILED DESCRIPTION OF THE PREFERRED EMBODIMENTS

The present disclosure will now be described in detail with reference to a few preferred embodiments thereof as illustrated in the accompanying drawings. In the following description, numerous specific details are set forth in order to provide a thorough understanding of the present disclosure. It will be apparent, however, to one skilled in the art, that the present disclosure may be practiced without some or all of these specific details. In other instances, well known process steps and/or structures have not been described in detail in order to not unnecessarily obscure the present disclosure.

An embodiment relies on absolute measurements of $SiF_4$ or $SiBr_4$, or $SiCl_4$ or other $SiX_4$ by-products that is a direct by-product of most silicon containing etches (nitrides, oxides, poly, and silicon films) when using fluorocarbon based chemistries. By combining the measurement with an etch model ($SiF_4$ mass balance based on XSEM images or a feature profile simulation model calibrated with XSEM images), one can predict endpoint, ER as a function of depth, average wafer selectivity, and uniformity in certain conditions. The $SiF_4$ by-products are detected using IR absorption using quantum cascade laser spectroscopy allowing parts per billion level detection for accurate predictions.

This disclosure describes a method and apparatus that combines etch-profile modeling coupled with $SiF_4$ IR-absorption to control the etch process. The method allows the extension of endpoint capability beyond the reach of traditional methods, such as emission spectroscopy, in high-aspect ratio applications such as DRAM cell-etch and 3D-NAND hole and trench patterning. The combination of absolute density measurement and etch profile emission modeling allows one to additionally determine in-situ etch process parameters such as ER, selectivity, and uniformity that can be used to achieve run-to-run process matching.

In an embodiment, an etch process is characterized by measuring a direct stable by-product that can be used to determine: 1) Endpoint for high-aspect ratio DRAM and 3D-NAND etches for process/CD control, 2) Method to scale endpoint detection for future nodes, 3) Combined with a model one can determine in-situ: a) Average wafer ER and ER as function of depth (ARDE), b) An average wafer uniformity and selectivity, and c) Both measurements can be used for run-to-run matching and fault detection, 4) Using high sensitivity quantum cascade laser spectroscopy to achieve ppb level limit of detection needed for accurate etch endpoint and etch parameters estimation.

Figure 1:
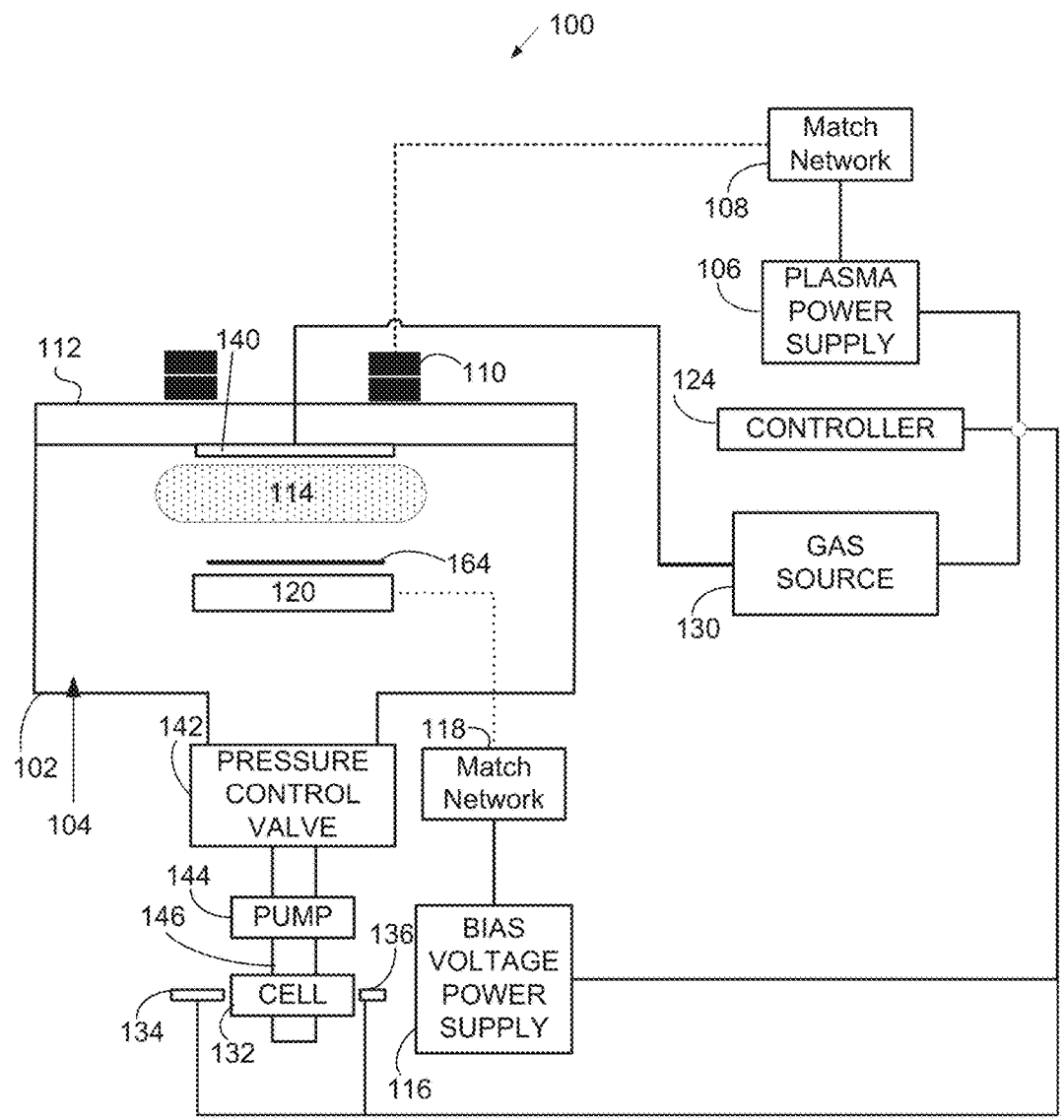
FIG. 1 schematically illustrates an example of a plasma processing chamber that may be used in an embodiment.

FIG. 1 schematically illustrates an example of a plasma processing chamber 100, which may be used to perform the process of etching a silicon containing layer in accordance with one embodiment. The plasma processing chamber 100 includes a plasma reactor 102 having a plasma processing confinement chamber 104 therein. A plasma power supply 106, tuned by a match network 108, supplies power to a TCP coil 110 located near a power window 112 to create a plasma 114 in the plasma processing confinement chamber 104 by providing an inductively coupled power. The TCP coil (upper power source) 110 may be configured to produce a uniform diffusion profile within the plasma processing confinement chamber 104. For example, the TCP coil 110 may be configured to generate a toroidal power distribution in the plasma 114. The power window 112 is provided to separate the TCP coil 110 from the plasma processing confinement chamber 104 while allowing energy to pass from the TCP coil 110 to the plasma processing confinement chamber 104. A wafer bias voltage power supply 116 tuned by a match network 118 provides power to an electrode 120 to set the bias voltage on the substrate 164 which is supported by the electrode 120. A controller 124 sets points for the plasma power supply 106, gas source/gas supply mechanism 130, and the wafer bias voltage power supply 116. The electrode 120 is used to support a substrate 164 in the plasma processing confinement chamber 104.

The plasma power supply 106 and the wafer bias voltage power supply 116 may be configured to operate at specific radio frequencies such as, for example, 13.56 MHz, 27 MHz, 2 MHz, 60 MHz, 200 kHz, 2.54 GHz, 400 kHz, and 1 MHz, or combinations thereof. Plasma power supply 106 and wafer bias voltage power supply 116 may be appropriately sized to supply a range of powers in order to achieve desired process performance. For example, in one embodiment, the plasma power supply 106 may supply the power in a range of 50 to 5000 Watts, and the wafer bias voltage power supply 116 may supply a bias voltage of in a range of 20 to 2000 V. For a bias up to 4 kV or 5 kV a power of no more than 25 kW is provided. In addition, the TCP coil 110 and/or the electrode 120 may be comprised of two or more sub-coils or sub-electrodes, which may be powered by a single power supply or powered by multiple power supplies.

As shown in FIG. 1, the plasma processing chamber 100 further includes a gas source/gas supply mechanism 130. The gas source 130 is in fluid connection with plasma processing confinement chamber 104 through a gas inlet, such as a shower head 140. The gas inlet may be located in any advantageous location in the plasma processing confinement chamber 104, and may take any form for injecting gas. Preferably, however, the gas inlet may be configured to produce a "tunable" gas injection profile, which allows independent adjustment of the respective flow of the gases to multiple zones in the plasma process confinement chamber 104. The process gases and by-products are removed from the plasma process confinement chamber 104 via a pressure control valve 142 and a pump 144, which also serve to maintain a particular pressure within the plasma processing confinement chamber 104. The gas source/gas supply mechanism 130 is controlled by the controller 124. A Kiyo by Lam Research Corp. of Fremont, Calif., may be used to practice an embodiment. In other examples, a Flex by Lam Research Corp. of Fremont, Calif., which uses capacitive coupling, may be used to practice an embodiment.

In this embodiment, connected to an exhaust pipe 146 after the pump 144, a gas cell 132 is provided, into which exhaust gas flows. A light source 134 is positioned adjacent to a window in the gas cell 132, so that a light beam from the light source 134 is directed into the gas cell 132. The light beam can travel through the gas cell multiple times (typically for a distance greater than 1 m) to achieve ppb level or even lower hundredth of ppt detection limits. The light is absorbed by the gas as it travels inside the gas cell. A light detector 136 is positioned adjacent to another window in the gas cell 132 to measure the light absorption level. In another embodiment, the light detector 136 may be placed adjacent to the light source 134 so that the same window may be used for the light detector 136 and the light source 134.

Figure 2:
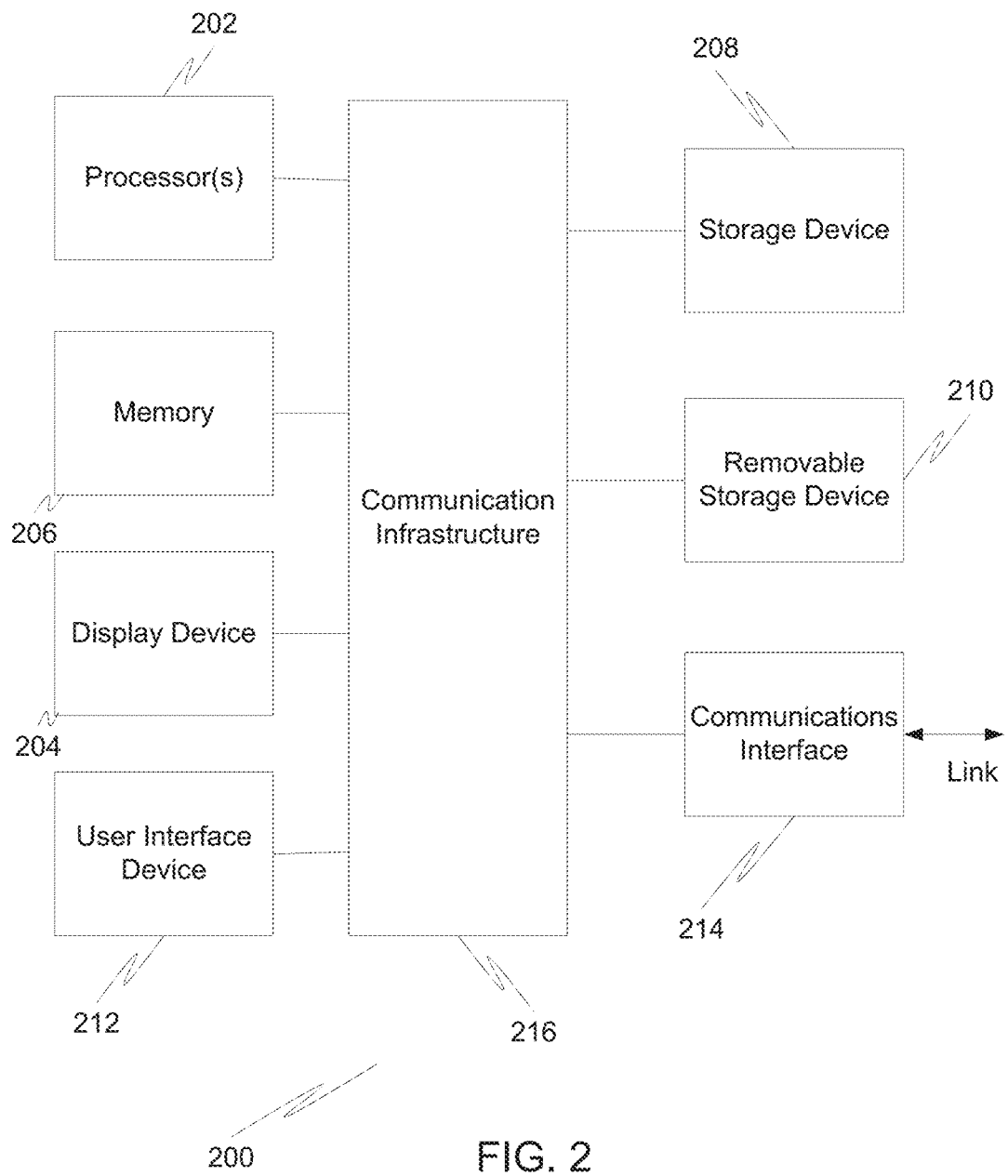
FIG. 2 is a high level block diagram showing a computer system, which is suitable for implementing a controller.

FIG. 2 is a high level block diagram showing a computer system 200, which is suitable for implementing a controller 124 used in embodiments. The computer system may have many physical forms ranging from an integrated circuit, a printed circuit board, and a small handheld device up to a huge super computer. The computer system 200 includes one or more processors 202, and further can include an electronic display device 204 (for displaying graphics, text, and other data), a main memory 206 (e.g., random access memory (RAM)), storage device 208 (e.g., hard disk drive), removable storage device 210 (e.g., optical disk drive), user interface devices 212 (e.g., keyboards, touch screens, keypads, mice or other pointing devices, etc.), and a communication interface 214 (e.g., wireless network interface). The communication interface 214 allows software and data to be transferred between the computer system 200 and external devices via a link. The communication interface 214 may also be used to adjust or change settings of the system to monitor it and optimize its live performance. The system may also include a communications infrastructure 216 (e.g., a communications bus, cross-over bar, or network) to which the aforementioned devices/modules are connected.

Information transferred via communications interface 214 may be in the form of signals such as electronic, electromagnetic, optical, or other signals capable of being received by communications interface 214, via a communication link that carries signals and may be implemented using wire or cable, fiber optics, a phone line, a cellular phone link, a radio frequency link, and/or other communication channels. With such a communications interface, it is contemplated that the one or more processors 202 might receive information from a network, or might output information to the network in the course of performing the above-described method steps.

Furthermore, method embodiments may execute solely upon the processors or may execute over a network such as the Internet in conjunction with remote processors that shares a portion of the processing.

The term "non-transient computer readable medium" is used generally to refer to media such as main memory, secondary memory, removable storage, and storage devices, such as hard disks, flash memory, disk drive memory, CD-ROM and other forms of persistent memory and shall not be construed to cover transitory subject matter, such as carrier waves or signals. Examples of computer code include machine code, such as produced by a compiler, and files containing higher level code that are executed by a computer using an interpreter. Computer readable media may also be computer code transmitted by a computer data signal embodied in a carrier wave and representing a sequence of instructions that are executable by a processor.

Figure 3:
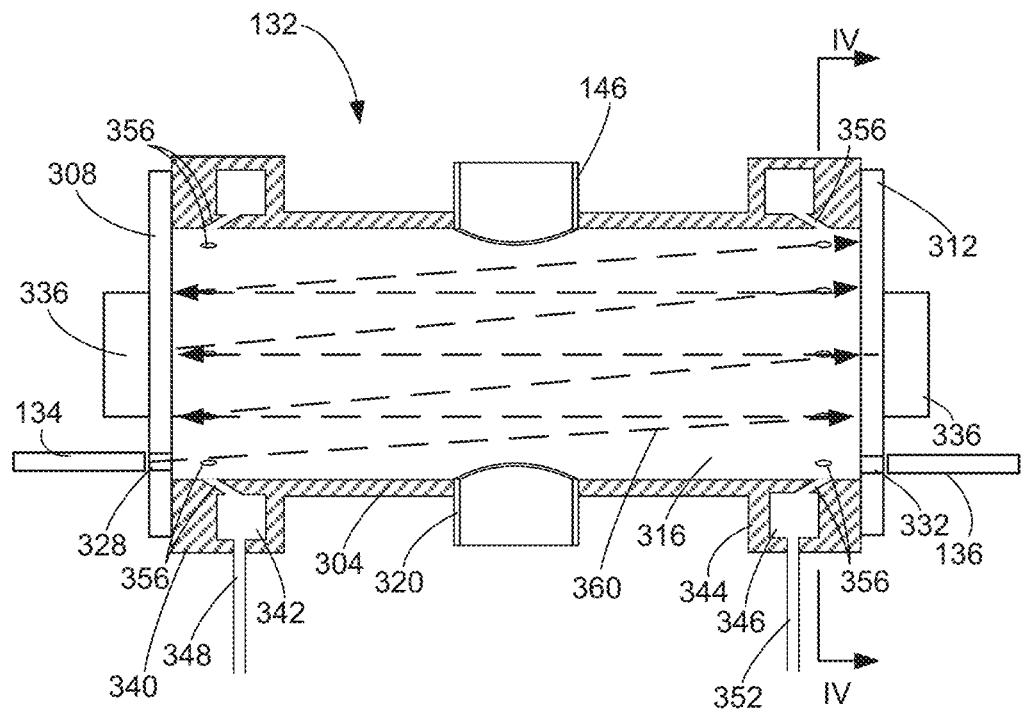
FIG. 3 is a more detailed schematic view of the gas cell of the embodiment, shown in FIG. 1.

FIG. 3 is a more detailed schematic view of the gas cell 132 of the embodiment, shown in FIG. 1. The exhaust pipe 146 extends from the output of pump. The gas cell 132 comprises a gas chamber 304, a first mirror 308, and a second mirror 312. The gas chamber 304, the first mirror 308, and the second mirror 312 define an optical cavity 316. The exhaust pipe 146 causes exhaust to flow into the optical cavity 316 in the gas chamber 304 and then out of the optical cavity 316 through an output port 320. In this embodiment the flow of the exhaust into and out of the optical cavity 316 is along a linear path. A light source 134, which in this embodiment is a quantum cascade laser (QCL) IR light source, is provided adjacent to a window 328 in the first mirror 308. An output fiber 332 is optically connected between a light detector 136, which is an IR detector, and the optical cavity 316 through the second mirror 312. The light can be coupled directly into the gas cell or through optical fibers. Heaters 336 are placed adjacent to the first mirror 308 and the second mirror 312. One or more of the heaters 336 may have heat sensors. The heaters 336 may be electrically connected to and controlled by the controller and may provide temperature data to the controller. A first purge ring 340 with a first purge ring channel 342 and a second purge ring 344 with a second purge ring channel 346 are provided, which surround the gas chamber 304. The first purge ring 340 is adjacent to the first mirror 308 and has a first purge gas input 348. The second purge ring 344 is adjacent to the second mirror 312 and has a second purge gas input 352. The first purge ring 340 and the second purge ring 344 are in fluid communication with the gas cell 132 and optical cavity 316 through a plurality of purge gas nozzles 356.

Figure 4:
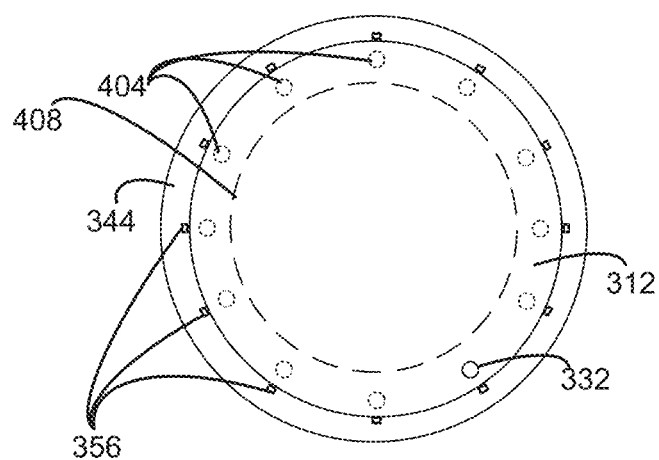
FIG. 4 is a cross-sectional view of a second purge ring and second mirror of FIG. 3 along cut line IV-IV.

FIG. 4 is a cross-sectional view of the second purge ring 344 and second mirror 312 of FIG. 3 along cut line IV-IV. In this example, twelve purge gas nozzles 356 are provided by the second purge ring 344. In this example, the light source, first mirror, second mirror, and light detector are positioned so that a light beam is directed to the second mirror 312 at twelve illumination areas 404, where one of the illumination areas is at the output fiber 332. In this example, the illumination areas 404 are in a ring around a circumference of the second mirror 312. The twelve purge gas nozzles 356 are positioned to selectively direct purge gas to the illumination areas with respect to other areas of the second mirror 312. For example, the central area 408 of the second mirror 312 does not have any illumination areas, so that the purge gas reaching the illumination areas 404 is at a greater pressure than the purge gas reaching the central area 408. FIG. 3 illustrates how a light beam 360 is reflected multiple times between the first mirror 308 and the second mirror 312 between the illumination areas. In this example, the reflections make a circle using the illumination areas.

Figure 5:
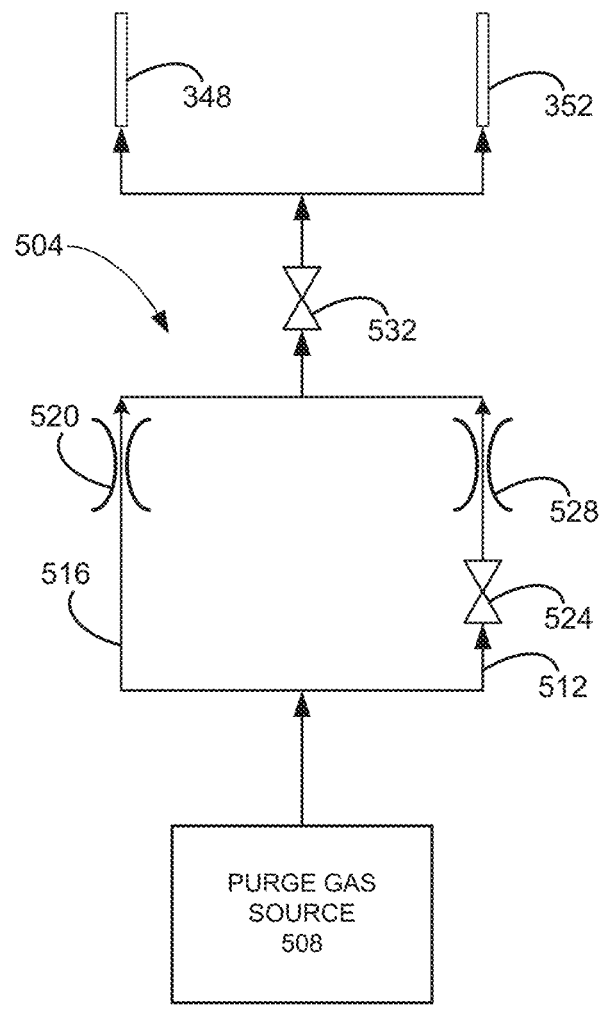
FIG. 5 is a schematic view of a purge gas system used in an embodiment.

FIG. 5 is a schematic view of a purge gas system 504 used in an embodiment. The purge gas system 504 comprises a purge gas source 508, a high flow line 512, a low flow line 516, which is at least partially parallel to the high flow line 512, and at least one switch for switching the flow between the high flow line 512 and the low flow line 516 to provide a low flow and a pulsed high flow. In this embodiment, the low flow line 516 comprises a low flow orifice 520 that provides a low flow. The high flow line 512 comprises a high flow line valve 524 and a high flow orifice 528. The low flow line 516 and the high flow line 512 are at least partially parallel and then merge and provide input to a valve 532. The output of the valve 532 is split and provided as input to the first purge gas input 348 and the second purge gas input 352. In this embodiment, the high flow line valve 524 and the valve 532 may be used as a switch for switching flow between the high flow line and the low flow line to provide a low flow and pulsed high flow. In this example, switching to the high flow line 512 allows purge gas to continue to flow through the low flow line 516. However, since the high flow line 512 has a greater flow, the high flow line 512 is dominant. In this example, the low flow orifice 520 provides a low flow of 300 sccm and the high flow orifice 528 provides a high flow of 3000 sccm. Either the high flow line valve 524 or the combination of the high flow line valve 524 and valve 532 may be used to provide a switch or flow controller for switching flow between a high flow and a low flow to provide a pulsed high flow.

In operation, a substrate is processed in the plasma processing chamber 100. In an example, a silicon containing layer is etched creating a silicon containing by-product gas. The silicon containing by-product gas is pumped out as exhaust by the pump into the optical cavity 316. The light source 134 provides a light beam 360 into the optical cavity 316 which is reflected multiple times between the first mirror 308 and the second mirror 312 at illumination areas 404 and then directed to the light detector 136. The light detector 136 provides an output to the controller 124, which uses the output to determine etch process parameters such as etch rate (ER), selectivity, and uniformity that can be used to achieve run-to-run process matching. In this example, the controller 124 is used as a measurement controller, which uses input from the light detector 136 to determine concentration of gas by-product, which is used to determine etch process parameters. During this process the purge gas system 504 provides a low flow jet of $N_2$ purge gas through the purge gas nozzles 356 to the illumination areas 404, to prevent dust, particles, and by-products from reaching the illumination areas, since dust, particles, and by-product would diffract light and lower reflectivity or transmission properties of the optical elements. A pulsed high flow of the $N_2$ purge gas may be provided to further clean the illumination areas. The determined process parameters are used to change the process recipe.

In various embodiments, the purge gas may be $N_2$, Ar, and air. $N_2$ is a preferred etch gas, since $N_2$ is inexpensive. If air is used, the air should be purified and the humidity should be removed. In some embodiments, the optical elements may be windows, which protect a mirror, where illumination areas are the points on the windows to which light is directed and through which light passes to and from a mirror. Various embodiments may provide purge gas flow rates between 150 sccm to 6000 sccm depending on the contamination due to previously run processes. The embodiment, allows sufficient cleaning with a flow rate of less than 6000 sccm. More preferably sufficient cleaning is provided with a flow rate of less than 3000 sccm. By providing cleaning below a maximum flow rate, additional pumps are not needed to provide the desired cleaning. Preferably, the high flow line provides a higher flow rate of purge gas than the flow rate of the purge gas of the low flow line. More preferable, the high flow line provides a flow rate of purge gas that is more than twice the flow rate of the purge gas of the low flow line. Most preferable, the high flow line provides a flow rate of purge gas that is more than 5 times the flow rate of the purge gas of the low flow line.

The purge gas is selectively directed to the illumination areas 404. The low flow of the purge gas may be used to selectively prevent contaminants from depositing on the illumination areas 404, which prevents degradation of the optical properties of the illumination areas 404. The high flow pulse of the purge gas may be used to provide additional cleaning and removal of deposits on the illumination areas 404. In one embodiment, the low flow may be constant and the high flow may be pulsed. In another embodiment, both the low and the high flow may be pulsed.

In this embodiment, the reflectivity of the illumination areas is critical for consistent process end call out. If the illumination areas are contaminated with particles, the reflectivity decreases causing sensitivity to decrease and the end process cannot be detected. This embodiment allows the cleaning and maintaining of the illumination areas 404 without breaking the vacuum.

In this embodiment, the light source 134 is an IR light source. The light detector 136 is an IR light detector. The first mirror 308 and second mirror 310 are IR optical elements that are reflective of IR light. Preferably, the light is IR light, for detecting Si containing by-products. In other embodiments, the light source 134 may be a visible or UV light source for providing visible or UV light. The light detector 136 would be a visible or UV light detector. The mirrors would reflect visible or UV light. The first mirror 308 provides a first optical element and the second mirror 310 provides a second optical element in this embodiment.

Figure 6:
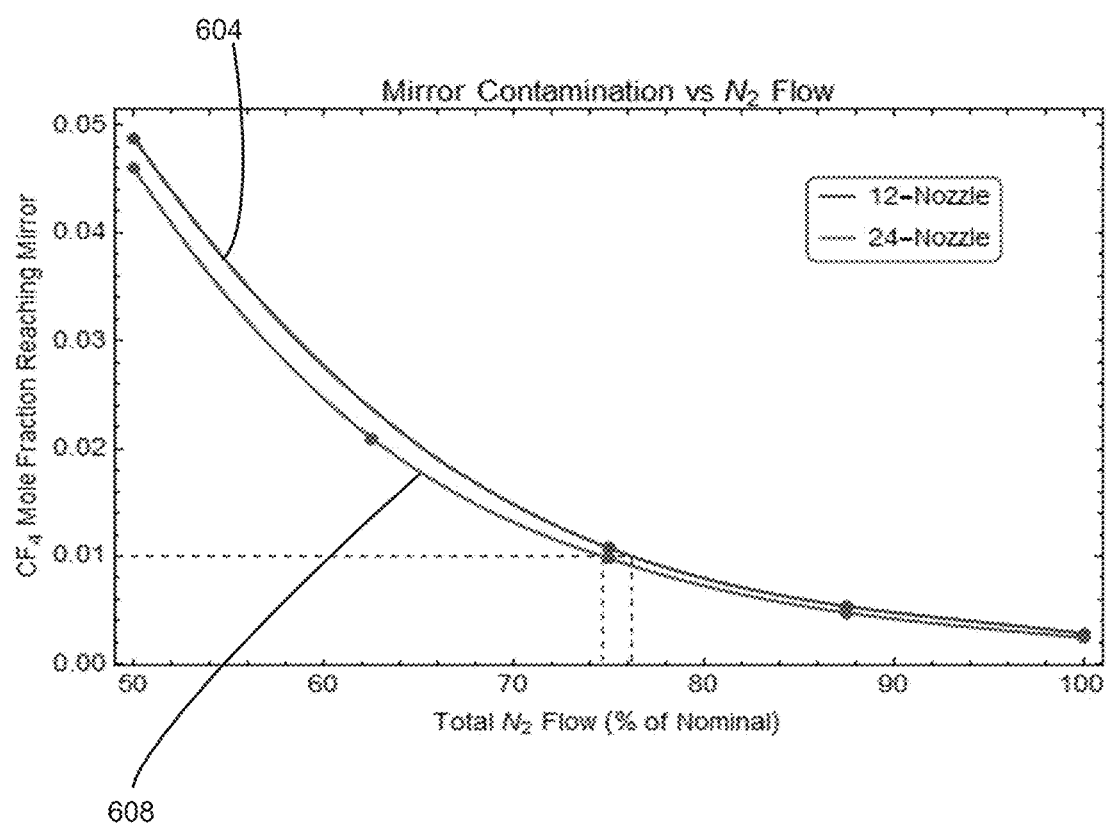
FIG. 6 is a graph illustrating a test of the above embodiment with 12 nozzles compared to an embodiment with 24 nozzles, where 24 illumination areas are used.

FIG. 6 is a graph illustrating a test of the above embodiment with 12 nozzles compared to an embodiment with 24 nozzles, where 24 illumination areas are used. The graph shows a first curve 604, which is plot of $CF_4$ mole fraction reaching the mirror versus total $N_2$ flow for 12 nozzles. The second curve 608 shows the same plot for 24 nozzles. As can be seen from the graph, providing 24 nozzles does not provide much of an advantage over providing 12 nozzles. As a result, preferably, only 12 nozzles are provided for 24 illumination areas. The experiments found that 300 sccm of $N_2$ purge gas was sufficient to maintain the mirrors at the required quality. The simulation used $CF_4$ as a heavy gas to see if particle dust can be repelled. Experiments found that the illumination areas were selectively maintained compared to other regions of the mirror. By only cleaning specific areas of the mirror the flow of gas may be reduced, while maintaining optical quality. FIG. 3 shows that the purge gas nozzles 356 are angled so that a jet of purge gas from the nozzle makes about a 60° angle with the surface of the mirrors. Various experiments have found that angling the nozzles so that the purge gas flow impacts the illumination areas at an angle between 30° and 80° allows for sufficient cleaning, while maintaining a minimal flow.

Experiments have also found that the heaters 336 should maintain the mirror surface at a temperature of greater than 90° C., in order to prevent depositions to maintain the illumination areas at the desired optical quality. More preferably, the heater maintains the mirror surface at a temperature of greater than 100° C. without causing any mechanical deformation that would otherwise disturb the optical cavity. In one example, the heater may be a resistance heater. In various embodiments, different heating zones may be provided, where the heaters heat different heating zones to different temperatures. For example, a zone containing the illumination areas may be heated to a higher temperature than a zone that does not contain the illumination areas.

FIG. 7 is a top view of another embodiment. This embodiment shows a ring shaped mirror 704 forming a sidewall of a cylinder. The gas chamber, not shown, forms a top and bottom of the cylinder and connects to the exhaust pump and output port. A light source 134 and light detector 136 are positioned adjacent to a window in the ring shaped mirror 704. In this embodiment, the light beam 708 forms a star shaped pattern in going from the light source 134 to the light detector 136. The number of reflections is controlled by the input angle of the light, and the light path may have a star polygon shape.

Other star shaped paths, such as eight or ten pointed stars may be used to increase the path length. In other embodiments, a vertical path may be combined with a star path, to create a helical path.

The measurement of by-product after the by-product has passed through an exhaust system, allows for the measurement to be performed at a higher pressure, when the by-product is more concentrated. This provides an advantage, when the plasma processing chamber is operated at a low pressure. Some plasma processing systems may operate at much higher pressure, such as the SELIS and Syndion manufactured by Lam Research of Fremont, Calif. Such higher pressure chambers would allow by-product measurement, gas purging, and optical element heating within the processing chamber.

Various embodiments are useful for providing memory devices such as DRAM and 3D-NAND devices. In various embodiments the plasma process is an etch process of a silicon containing layer or a low-k dielectric layer. In various embodiments the RF power may be inductively coupled or capacitively coupled. In other embodiments, alternating layers of silicon oxide and polysilicon (OPOP) or silicon oxide and silicon nitride (ONON) may be etched.

While this disclosure has been described in terms of several preferred embodiments, there are alterations, permutations, modifications, and various substitute equivalents, which fall within the scope of this disclosure. It should also be noted that there are many alternative ways of implementing the methods and apparatuses of the present disclosure. It is therefore intended that the following appended claims be interpreted as including all such alterations, permutations, and various substitute equivalents as fall within the true spirit and scope of the present disclosure.

What is claimed is:

1. A gas exhaust by-product measurement system, attachable to an exhaust output from an exhaust pump of a processing chamber, comprising:
   a gas chamber configured to receive exhaust from the exhaust output, the gas chamber further including an optical cavity, wherein the exhaust passes through the optical cavity;
   at least one optical element;
   a light source;
   a light detector, wherein the at least one optical element, light source, and light detector are positioned so that a light beam from the light source is directed to the at least one optical element a plurality of times before reaching the light detector;

at least one heater for providing heat to the at least one optical element, so that the at least one optical element is heated by the at least one heater;

a purge gas source;

a plurality of purge gas nozzles in fluid connection with the optical cavity;

a high flow line in fluid connection between the purge gas source and the plurality of purge gas nozzles;

a low flow line in fluid connection between the purge gas source and the plurality of purge gas nozzles, wherein at least part of the low flow line is in parallel to the high flow line; and at least one flow controller for managing a plurality of flow rates including a high flow and a low flow.

2. The gas exhaust by-product measurement system, as recited in claim 1, wherein the at least one optical element includes a first optical element wherein the light beam is directed to a plurality of illumination areas on the first optical element, and wherein the plurality of purge gas nozzles selectively direct purge gas to the plurality of illumination areas on the first optical element.

3. The gas exhaust by-product measurement system, as recited in claim 1, wherein the at least one optical element includes a mirror.

4. The gas exhaust by-product measurement system, as recited in claim 1, wherein the purge gas source provides a gas comprising at least one of $N_2$, Ar, or air.

5. The gas exhaust by-product measurement system, as recited in claim 1, wherein the at least one optical element comprises a first optical element and a second optical element, wherein the first and second optical elements are spaced apart and wherein the optical cavity is between the first and second optical elements.

6. The gas exhaust by-product measurement system, as recited in claim 1, wherein the high flow is pulsed while the low flow is constant.

7. The gas exhaust by-product measurement system, as recited in claim 1, wherein the light source is an IR light source, the light detector is an IR detector, and the at least one optical element is an IR optical element.

8. The gas exhaust by-product measurement system, as recited in claim 1, wherein the at least one optical element includes a first optical element wherein the light beam is directed to a plurality of illumination areas disposed around a circumference of the first optical element, and wherein the plurality of purge gas nozzles selectively direct purge gas to the plurality of illumination areas on the first optical element.

9. The gas exhaust by-product measurement system, as recited in claim 1, wherein the at least one optical element includes a first optical element wherein the light beam is directed to a plurality of illumination areas on the first optical element, and wherein the plurality of purge gas nozzles selectively direct a purge gas from the purge has source to the plurality of illumination areas on the first optical element, wherein the purge gas selectively cleans the illumination areas.

10. The gas exhaust by-product measurement system, as recited in claim 1, wherein the at least one optical element includes a first optical element wherein the light beam is directed to a plurality of illumination areas on the first optical element, and wherein the plurality of purge gas nozzles selectively direct a purge gas from the purge gas source to the plurality of illumination areas on the first optical element, wherein the purge gas selectively cleans the illumination areas and reduces deposition on the illumination areas.

11. The gas exhaust by-product measurement system, as recited in claim 1, wherein the high flow is pulsed and the low flow is pulsed.

12. The gas exhaust by-product measurement system, as recited in claim 1, further comprising a measurement controller connected to receive input from the light detector, comprising:

at least one processor; and computer readable media, comprising:
  computer readable code for receiving input from the light detector; and
  computer readable code for determining gas by-product concentration from the input from the light detector.

13. A gas exhaust by-product measurement system, attachable to an exhaust output from an exhaust pump of a processing chamber, comprising a gas chamber configured to receive exhaust from the exhaust output, the gas chamber further including an optical cavity, wherein the exhaust passes through the optical cavity;

at least one optical element;

a light source;

a light detector, wherein the at least one optical element, light source, and light detector are positioned so that a light beam from the light source is directed to the at least one optical element a plurality of times before reaching the light detector;

at least one heater for providing heat to the at least one optical element, so that the at least one optical element is heated by the at least one heater;

a purge gas source that provides a purge gas flow of no more than 6000 sccm; and a plurality of purge gas nozzles in fluid connection between the optical cavity and the purge gas source.

14. The gas exhaust by-product measurement system, as recited in claim 13, wherein the purge gas source that provides a purge gas flow of no more than 3000 sccm.

15. The gas by-product measurement system, as recited in claim 13, wherein the light beam is directed to a plurality of illumination areas of the at least one optical element, and wherein the purge gas nozzles are selectively directed to the illumination areas.

16. The gas by-product measurement system, as recited in claim 13, wherein the light source is an IR light source, the light detector is an IR detector, and the at least one optical element is an IR optical element.

* * * * *